United States Patent [19]

Tsui et al.

[11] Patent Number: 5,023,371

[45] Date of Patent: Jun. 11, 1991

[54] SYNTHESIS OF THIOGLYCOLIC ACID

[75] Inventors: Mosum E. Tsui, Silver Spring; Martin B. Sherwin, Potomac, both of Md.

[73] Assignee: W. R. Grace & Co.-Conn., New York, N.Y.

[21] Appl. No.: 53,976

[22] Filed: May 26, 1987

Related U.S. Application Data

[63] Continuation of Ser. No. 655,586, Nov. 28, 1984, abandoned.

[51] Int. Cl.$^5$ .................. C07C 319/02; C07C 319/06; C07C 323/52
[52] U.S. Cl. ................................ 562/512; 562/592; 562/594
[58] Field of Search ........................................ 562/512

[56] References Cited

U.S. PATENT DOCUMENTS

| | | |
|---|---|---|
| 2,413,361 | 12/1946 | Martin . |
| 2,594,030 | 4/1952 | Coons et al. . |
| 3,860,640 | 1/1975 | Tamura et al. . |
| 3,860,641 | 1/1975 | Zengel et al. . |
| 3,927,085 | 12/1975 | Zengel et al. .................. 562/512 |
| 4,082,790 | 4/1978 | Speier .................. 560/260 |

FOREIGN PATENT DOCUMENTS

| | | | |
|---|---|---|---|
| 17564 | 7/1968 | Japan | .................. 562/512 |
| 29440 | 3/1976 | Japan | .................. 562/512 |
| 624568 | 11/1946 | United Kingdom | . |

OTHER PUBLICATIONS

Chemische Berichte, 39, 732–738 (1906), "Zur Kenntniss der Thioglykolsaure" by Klason et al.

Denbigh, K., Chemical Reaction Theory University Press, 1965, pp. 120–121.

*Primary Examiner*—Vivian Garner
*Attorney, Agent, or Firm*—Howard J. Troffkin

[57] ABSTRACT

A process for forming thioglycolic acid by contacting in a reaction zone at elevated pressure of at least 250 psig a mixture of monochloroacetic acid and dichloroacetic acid with a molar excess of an alkali metal hydrosulfide to form the alkali metal salt of thioglycolic acid, acidifying said salt and removing the free thioglycolic acid. A preferred process further requires separating any formed thiodiglycolic acid from the resultant liquid phase materials and recycling said acid to the reaction zone.

15 Claims, No Drawings

SYNTHESIS OF THIOGLYCOLIC ACID

This is a continuation of application Ser. No. 837,248, filed Mar. 7, 1986 now abandoned and Ser. No. 655,586, filed Sept. 28, 1984, now abandoned.

BACKGROUND OF THE INVENTION

The present invention is directed to a process for forming thioglycolic acid in high yields by reacting mixtures of monochloroacetic acid and dichloroacetic acid with an alkali metal hydrosulfide under conditions described herein below.

Thioglycolic acid is a highly desired product having various commercial applications. It forms the active ingredient of most hair waving preparations. It is also used extensively in cosmetic depilatories and in commercial agents used to remove hair from hides and the like. Various other commercial uses are made of thioglycolic acid in addition to those described above. The large and varied demands for thioglycolic acid provide a great need for forming this material in the most effective and economical method.

Thioglycolic acid is presently prepared commercially by reacting pure monochloroacetic acid with sodium hydrosulfide in an aqueous medium. After acidification, thiogylcolic acid is extracted from the reaction mixture with some suitable organic solvent and purified by distillation. This process was first described by Carius in Ann. 124, 43 (1862) and later improved by Klason and Carlson in Ber. 39, 732–738 (1906). The later authors taught that the process is best carried out using a sodium hydrosulfide liquor of not more than 15 percent by weight and a weak monochloroacetic acid solution containing the acid in not more than 20 percent by weight.

Alternate methods have been suggested. These include a two step synthesis of initially reacting monochloroacetic acid with sodium thiosulfate followed by hydrolysis of the resulting Bunte salt (See U.S. Pat. Nos. 2,594,030; 2,413,361 and British Patent No. 624,568). Another proposed synthesis (German Patent No. 180,875) involves the reaction of monochloroacetic acid with an alkali polysulfide and then reducing the formed dithiodiglycolic acid by means of zinc and mineral acid. U.S. Pat. No. 3,860,641 described a process of forming thioglycolic acid by heating an alkali hydrosulfide with a xanthogenic acid.

Recent patents directed to modifications of the Klason and Carlson process for forming thioglycolic acid include U.S. Pat. Nos. 3,927,085 and 4,082,790. U.S. Pat. No. 3,927,085 describes a modification which requires the presence of aqueous sodium or ammonium hydroxide, a partial pressure of hydrogen sulfide and pure monochloroacetic or monochloropropionic acid in 4–12 mol. percent.

U.S. Pat. No. 4,082,790 teaches that mono, di or tri mercaptans of the formula $R(SH)_a$ can be formed by reacting the corresponding mono, di or tri chloride or bromide, $R(X)_a$ with $H_2S$ and ammonia or an amine in aqueous systems to give the corresponding mercaptan $R(SH)_a$. R can represent an aliphatic carboxylic acid and a represents an integer of 1 to 3.

The process most commonly used is that described by Klason and Carlson. The starting carboxylic acid is pure monochloroacetic acid either as the free acid or as its alkali metal salt. The acid feed is required to be free of polyhalo acids to avoid the formation of the corresponding polythiols as suggested in U.S. Pat. No. 4,082,790. In view of the fact that the chloroacetic acid is normally formed as a mixture of mono and dihalo acids, the presently known art requires separation and purification of the monochloroacetic acid prior to its use in order to achieve high yields of the desired product.

It would be highly desired to have a process of forming the desired thioglycolic acid product which utilizes a combination of mono and polychloroacetic acids as feed reactant. Such a process would provide a more effective and economical mode of producing the desired product.

SUMMARY OF THE INVENTION

The present invention is directed to a process for forming thioglycolic acid in high yields by reacting, in an aqueous medium and under and elevated pressure of at least 250 psig provided by hydrogen sulfide, a mixture of monochloroacetic acid and dichloracetic acid or their alkali metal salts with alkali or alkaline earth metal hydrosulfide.

DETAILED DESCRIPTION OF THE INVENTION

The subject invention is directed to an effective process for forming thioglycolic acid in high yields by reacting, in an aqueous medium and under elevated pressure of at least 250 psig, a mixture of mono- and dichloroacetic acid with sodium hydrosulfide under the conditions described herein below. The present process provides a means of achieving very high yields of the desired product while using a mixture of chloride substituted acetic acids. This process eliminates the previously required purification of monochloroacetic acid for use as a feed in commercial formation of thioglycolic acid.

The halogenated organic acid feed used in the present process is a mixture of monochloroacetic acid and dichloroacetic acid. The weight ratio of mono to di substituted acetic acids in the feed can range from about 99:1 to 75:25 and from about 98:2 to 95:5 being preferred. The inclusion of the dichloroacetic acid as part of the feed has, under the present conditions, been unexpectedly found not to be detrimental to but, instead, to aid in producing thioglycolic acid in high yields.

The mixed organic acid feed can be introduced into the reaction zone, as described below, in aqueous medium. The concentration of the mixed organic acid feed can be any concentration which provides a homogeneous liquid phase under the reaction conditions. The organic acid feed can be from about 5 to 35 weight percent with from about 20 to 35 weight percent being preferred based on the aqueous liquid system introduced into the reaction zone.

The mixed organic acid feed can be introduced in the form of the free acids. The free acid is the preferred feed although the acids may be partially or totally in the form of their alkali metal, such as sodium, salt when introduced into the reaction zone.

The alkali or alkaline earth metal hydrosulfide reactant can be readily formed in known manners. It is preferred to use sodium hydrosulfide although other alkali metal hydrosulfides, such as potassium hydrosulfide, or alkaline earth metal hydrosulfides, such as calcium hydrosulfide, may be used. The alkali or alkaline earth metal hydrosulfide should be in water soluble concentrations of from 7 to about 40 weight percent and preferably from 25 to 35 weight percent in the aqueous system in the reaction zone.

The aqueous feeds of (1) the mixed chloroacetic acids and (2) the metal hydrosulfide should be introduced into the reaction zone so that there is a molar excess of the metal hydrosulfide to the mixed mono and di chloroacetic acids. The molar ratio of the metal hydrosulfide to monochloroacetic acid (as free acid) in the feed should be at least 2.1 or, when supplied as salt, should be at least 1.1. The molar ratio of metal hydrosulfide to dichloroacetic acid (as free acid) in the feed should be at least 3.1 and, if supplied as the salt, should be at least 2.1. Higher ratios can be used. The preferred molar ratio of metal hydrosulfide to monochloroacetic acid is from 2.1 to about 3 and the dichloroacetic acid is from 3.1 to about 4. Even higher ratios can be used.

The reaction is carried out at a pressure of at least 250 psig with pressures from 250 to about 500 being found to provide the best yields. It is critical that the reaction be conducted under the described elevated pressures of hydrogen sulfide to cause the process to produce the desired product in high yields. The pressure can be achieved by the autogeneous pressure of the reactants or with the addition of supplemental hydrogen sulfide gas.

In contrast to the criticality of elevated pressure conditions, it has been observed that when using the present reactants, the reaction can be carried out at low temperatures. The reaction can be carried out a temperatures ranging from ambient to about 150° C. and preferably from ambient to 100° C. and most preferably from ambient to 60° C. The ability to carry out the process at low temperatures is another beneficial aspect of the invention to unexpectedly provide an economically effective process.

The length of time for the reactants to be contained within the reaction zone can be readily determined by those skilled in this art in order to optimize the yield. Normally the time will vary depending upon the size and configuration of the reactor and whether the process is run in a batch or continuous mode. Normally residence times of at least about 20 minutes provides good yields with times greater than about 40 minutes showing substantially no further increase in yields. Greater or less times may be appropriate under varying reaction zone conditions.

The reaction zone can be any reactor capable of causing contact among the reactants in either a batch or continuous process mode. For example, a conventional tubular reactor or its equivalent can be used to carry out the reaction in a continuous manner while a pressure reaction vessel can be used for batch operation.

The feed streams (one containing a mixture of organic acids and one containing alkali metal hydrosulfide) can be mixed prior to entry into the reaction zone. Mixing may be accomplished by various conventional means for liquid-liquid mixing such as vortex mixers or static mixers with stainless steel gauze coils or the like. The mixed feeds are introduced into a reaction zone. When the process is carried out on a continuous basis, a high pressure metering pump or the like can be used to introduce the fluid feeds into the reaction zone at a rate so as to have the reactants maintained in the reaction zone for a residence time sufficient to permit the reactants to form thioglycolic acid product in high yields.

The reaction zone is required to be maintained at a pressure of at least 250 psig (preferably from 250 to 500 psig) and can be at temperatures ranging from ambient to about 150° C. (preferably ambient to 100° C. and most preferably from ambient to 80° C.) as described above.

The liquid material is removed from the reaction zone. For example, in a continuous process the removal can be effected by flashing the liquid through a back pressure regulator or the like to atmospheric pressure. The off gases which are produced in the reactor (mainly $H_2S$) are then removed and normally passed through caustic scrubbers.

The aqueous liquid removed from the reaction zone contains thioglycolic acid as the main (normally greater than 90% yield) reaction product and may also contain small amounts of thiodiglycolic acid as by-product. The liquid removed from the reaction zone can be treated with an inorganic mineral acid such as sulfuric acid to convert the organic acid alkali metal salts to the free acid material.

It has been further unexpectedly found that the major by-product, thiodiglycolic acid, can be removed, recycled and introduced into the reaction zone as part of the feed. When recycling the thiodiglycolic acid by-product under the process conditions of the present invention, one achieves overall yeilds of the desired product of about 95–100 percent. The formation of thioglycolic acid from the thiodiglycolic acid has been hypothesized to occur (this theory is not meant as a limitation on the subject invention but merely as a suggested mode) by the disproportionation of the thiodiglycolic acid according to the following reaction:

$NaOOCCH_2SCH_2COONa + H_2S \rightarrow 2HSCH_2COONa$

The following examples are given for illustrative purposes only and are not meant to be a limitation on the claims appended hereto. All parts and percentages are by weight unless otherwise indicated.

EXPERIMENTAL

The process was performed in a continuous manner using a tubular reactor. It consisted of a 17 ft. long, ⅛" ID × ¼" OD tubular reactor coiled in a spiral so that it fit into a high temperature oil bath. The temperature of the bath, $T_2$ and that of the product, $T_1$ were closely monitored by two thermocouples and controlled by an automatic temperature controller. The pressure of the reactor system was controlled by a back-pressure regulator with a range of 0–500 psi and was closely monitored by two pressure gauges, with a range of 0–600 psig, located at the entrance and exit of the tubular reactor. The alkali metal hydrosulfide (as NaSH) and the mixed mono and dichloroacetic acid feeds were introduced into the tubular reactor from reservoirs via separate dual-piston high pressure metering pumps with flow capacities from 0.12 ml/min to 3.6 ml/min per head. The feeds were initially mixed using a dual tube mixer. The NaSH stream was introduced through the insert charge tube with the organic acid stream coming from the outside. The two streams were then passed through a static mixer having coils of stainless steel gauze to achieve further mixing. The liquid phase product from the reactor was flashed through a back-pressure regulator to atmospheric pressure. It was then acidified with 75% sulfuric acid before being collected in a stainless steel receiver. The off gases were then passed through two caustic scrubbing solutions in series to remove the hydrogen sulfide. Samples of the liquid product were analyzed by standard technique for thioglycolic acid (TGA), thiodiglycolic acid (TDGA) and dithiodiglycolic acid (DTDGA) using high pressure liquid chromatography. The thioglycolic acid can be recovered by extraction using methylisobutylketone followed by distillation.

Using the apparatus described above a series of runs were conducted using a commercial mixture of monochloroacetic acid (MCA) and dichloroacetic acid (DCA) in a molar ratio of 97:3. The reactions were each run at a pressure of 400 psig (inlet and exit pressure) and a residence time of 40 minutes. The temperature of the runs were varied between 25° C. and 80° C. by monitering the reaction and exit temperature. The results of the runs are given in Table I below.

TABLE I

| Run | Temp. °C. | MCA | DCA molar conc. | NaSH | TGA | TDGA % yield | DTDGA |
|---|---|---|---|---|---|---|---|
| 1 | 25 | 3.0 | 0.09 | 6.6 | 91.4 | 4.5 | — |
| 2 | 50 | 3.0 | 0.09 | 6.6 | 87.3 | 6.3 | — |
| 3 | 80 | 3.0 | 0.09 | 6.6 | 90.3 | 8.6 | — |

EXAMPLE II

A series of runs were conducted in the same manner as described in Example I above except that the temperature was maintained at 25° C. while the pressure in the reaction zone was varied in each run. The results given in Table II below show that the present process must be carried out at elevated pressure of at least about 250 psig (primarily due to $H_2S$) to provide the desired thioglycolic acid in high yields. Reactions carried out at lower pressures (even at much longer reaction times) does not provide the high yields desired.

TABLE II

| Run | Temp. °C. | Pressure psig | Residence Time (min.) | Yield TGA % |
|---|---|---|---|---|
| 4 | 25 | 0 | 70 | 57 |
| 5 | 25 | 150 | 70 | 88 |
| 6 | 25 | 250 | 40 | 92 |
| 7 | 25 | 400 | 40 | 95 |

EXAMPLE III

A series of runs is conducted in the same manner as described in Example I above except that the thioether of glycolic acid (TDGA) is recovered as the still bottom from the distillation and recovery of the thioglycolic acid. The recovered thioether is introduced back into the reaction zone as part of the mixed organic acid feed stream. The resultant overall yield of thioglycolic acid product is increased by about 3.5 to 5 percent.

We claim:

1. A process for forming thioglycolic acid comprising contacting in a reaction zone at a temperature of from ambient to about 150° C. and under an elevated pressure of at least 250 psig formed by hydrogen sulfide gas, a mixture of monochloroacetic acid and dichloroacetic acid or their alkali metal salts in a weight ratio of from 99:1 to 75:25 with an alkali or alkaline earth metal hydrosulfide such that the molar ratio of said metal hydrosulfide to monochloroacetic acid as free acid is at least 2.1 and to dichloroacetic acid is at least 3.1; separating the liquid products and recovering the thioglycolic acid therefrom.

2. The process of claim 1 wherein the molar ratio of monochloroacetic to dichloroacetic acid is from 98:2 to 95:5.

3. The process of claim 1 further comprising separating and recovering thiodiglycolic acid from the reaction zone liquid products and reintroducing at least a portion of the recovered thiodiglycolic acid to the reaction zone.

4. The process of claim 1 wherein the reaction zone is at a temperature of from ambient to about 100° C.

5. The process of claim 4 wherein the molar ratio of monochloroacetic to dichloroacetic acid is from 98:2 to 95:5.

6. The process of claim 4 further comprising separating and recovering thiodiglycolic acid from the reaction zone liquid products and reintroducing at least a portion of the recovered thiodiglycolic acid to the reaction zone.

7. The process of claim 1 wherein the ratio of the metal hydrosulfide to the combined mixture of mono and dichloroacetic acid is from 2.1 to about 3 with respect to the monochloroacetic acid component and from 3.1 to about 4 for the dichloroacetic acid component.

8. The process of claim 7 wherein the molar ratio of monochloroacetic to dichloroacetic acid is from 98:2 to 95:5.

9. The process of claim 7 further comprising separating and recovering thiodiglycolic acid from the reaction zone liquid products and reintroducing at least a portion of the recovered thiodiglycolic acid to the reaction zone.

10. The process of claim 1 wherein the reaction zone pressure is from 250 to 500 psig.

11. The process of claim 10 wherein the reaction zone is at a temperature of from ambient to about 100° C.

12. The process of claim 11 wherein the molar ratio of monochloroacetic to dichloroacetic acid is from 98:2 to 95:5.

13. The process of claim 11 further comprising separating and recovering thiodiglycolic acid from the reaction zone liquid products and reintroducing at least a portion of the recovered thiodiglycolic acid to the reaction zone.

14. A process for forming thioglycolic acid comprising contacting in a reaction zone under elevated pressure of from at least 250 psig to 500 psig formed by hydrogen sulfide gas and at a temperature of from ambient to 80° C. a mixture of monochloroacetic acid and dichloroacetic acid or their alkali salts in a weight ratio of from 99:1 to 75:25 with an alkali metal hydrosulfide such that the molar ratio of metal hydrosulfide to the monochloroacetic acid of said mixture is at least 2.1 and to the dichloroacetic acid is at least 3.1, separating and recovering thioglycolic acid from the liquid product of the reaction zone.

15. The process of claim 14 wherein the ratio of mono- to dichloroacetic acid is 98:2 to 95:5, the alkali metal hydrosulfide is sodium hydrosulfide, the molar ratio of metal hydrosulfide to monochloroacetic acid is from 2.1 to 3, the molar ratio of metal hydrosulfide to dichloroacetic acid is 3.1 to 4, and further separating and recovering thiodiglycolic acid from the liquid product of the reaction zone and reintroducing at least a portion of the recovered thiodiglycolic acid to the reaction zone.

* * * * *